US012678596B2

(12) United States Patent

Penalba Corpas

(10) Patent No.: US 12,678,596 B2
(45) Date of Patent: Jul. 14, 2026

(54) DEVICE FOR SECURING A PERIPHERAL VENOUS CATHETER

(71) Applicant: STABLE U MEDICAL DEVICES, S.L., Madrid (ES)

(72) Inventor: Miguel Angel Penalba Corpas, Torremolinos (ES)

(73) Assignee: STABLE U MEDICAL DEVICES, S.L., Madrid (ES)

( * ) Notice: Subject to any disclaimer, the term of this patent is extended or adjusted under 35 U.S.C. 154(b) by 846 days.

(21) Appl. No.: 17/642,197

(22) PCT Filed: Sep. 9, 2020

(86) PCT No.: PCT/ES2020/070530
§ 371 (c)(1),
(2) Date: Mar. 10, 2022

(87) PCT Pub. No.: WO2021/048457
PCT Pub. Date: Mar. 18, 2021

(65) Prior Publication Data
US 2022/0313954 A1      Oct. 6, 2022

(30) Foreign Application Priority Data

Sep. 10, 2019    (ES) .................................... 201930788

(51) Int. Cl.
*A61M 25/02* (2006.01)
*A61M 5/14* (2006.01)
(Continued)

(52) U.S. Cl.
CPC ........... *A61M 25/02* (2013.01); *A61M 5/1418* (2013.01); *A61M 2005/1586* (2013.01);
(Continued)

(58) Field of Classification Search
CPC .......... A61M 25/02; A61M 2025/0253; A61M 2025/0213; A61M 2025/024;
(Continued)

(56) References Cited

U.S. PATENT DOCUMENTS 3,059,645 A * 10/1962 Hasbrouck ............ A61M 25/02
604/179
3,630,195 A * 12/1971 Santomieri ........... A61M 25/02
24/336
(Continued)

FOREIGN PATENT DOCUMENTS

CN          103239790 B     2/2015
WO       2006026290 A2     3/2006
(Continued)

OTHER PUBLICATIONS

International search report for PCT/ES2020/070530 (2 pages).
China Search Report, CN202080062492.0, Dec. 11, 2023.
European Search Report EP 20862104.5, Oct. 10, 2023, 8 pages.

*Primary Examiner* — William R Carpenter
*Assistant Examiner* — Robert F Allen
(74) *Attorney, Agent, or Firm* — Darrell Mottley

(57) ABSTRACT

A device for securing a peripheral venous catheter, including a body comprising first and second fastening extremities and a connecting section that interconnects said fastening extremities, the latter feature a tubular shape and comprising corresponding first and second longitudinal grooves; a portion of the catheter may be inserted through said grooves to grasp the same in a folded manner, the connecting section comprises first and second portions extending between the longitudinal grooves, in such a way that the fastening extremities and the portions of the connecting section form a closed perimeter outline defining a hollow internal space adapted to be set between an open position and a closed position, where, the hollow internal space being open, the (Continued)

portion of the catheter may be inserted for the attachment thereof to the fastening extremities, and then secured to the latter when the hollow internal space is closed.

12 Claims, 3 Drawing Sheets

(51) Int. Cl.
　　*A61M 25/01* 　　　　(2006.01)
　　*A61M 5/158* 　　　　(2006.01)
(52) U.S. Cl.
　　CPC ..... *A61M 25/01* (2013.01); *A61M 2025/0206* (2013.01); *A61M 2025/0246* (2013.01); *A61M 2025/0253* (2013.01); *A61M 2025/0266* (2013.01); *A61M 2025/028* (2013.01)
(58) Field of Classification Search
　　CPC ...... A61M 2025/028; A61M 2039/087; A61M 2025/0246; A61M 2025/0266; A61M 5/1418; A61M 2025/0206; A61M 25/01; A61M 2005/1586
　　See application file for complete search history.

(56) References Cited

U.S. PATENT DOCUMENTS

| | | | | |
|---|---|---|---|---|
| 3,834,380 | A * | 9/1974 | Boyd | A61M 25/02 |
| | | | | 128/DIG. 26 |
| 4,453,933 | A * | 6/1984 | Speaker | A61M 25/02 |
| | | | | 128/877 |
| 4,919,654 | A | 4/1990 | Kalt | |
| 5,269,803 | A * | 12/1993 | Geary | A61B 17/1322 |
| | | | | 606/201 |
| 5,643,216 | A | 7/1997 | White | |
| 5,702,371 | A * | 12/1997 | Bierman | A61M 39/1011 |
| | | | | 604/174 |
| 5,947,931 | A | 9/1999 | Bierman | |
| 6,001,081 | A | 12/1999 | Collen | |
| 6,685,670 | B2 * | 2/2004 | Miles | A61M 5/142 |
| | | | | 604/80 |
| 8,911,396 | B2 * | 12/2014 | Gordon | A61M 25/0097 |
| | | | | 604/93.01 |
| 9,717,885 | B1 * | 8/2017 | Narciso Martinez . | A61M 25/02 |
| 10,835,666 | B2 * | 11/2020 | Amir | C09J 7/30 |
| 2001/0049504 | A1 * | 12/2001 | Gautsche | A61B 46/23 |
| | | | | 604/179 |
| 2006/0047268 | A1 * | 3/2006 | Stephens | A61M 25/0041 |
| | | | | 604/533 |
| 2009/0254040 | A1 * | 10/2009 | Bierman | A61M 25/02 |
| | | | | 604/174 |
| 2009/0306603 | A1 | 12/2009 | Bierman et al. | |
| 2010/0114034 | A1 * | 5/2010 | Wright | A61M 25/02 |
| | | | | 604/177 |
| 2013/0165863 | A1 * | 6/2013 | Nilson | A61M 25/02 |
| | | | | 604/174 |
| 2013/0211382 | A1 * | 8/2013 | Mouri | A61M 25/0133 |
| | | | | 604/95.01 |
| 2014/0343531 | A1 * | 11/2014 | Larkin | A61M 25/02 |
| | | | | 604/174 |
| 2019/0160262 | A1 * | 5/2019 | Jones | A61M 25/02 |

FOREIGN PATENT DOCUMENTS

| | | |
|---|---|---|
| WO | 2011084505 A2 | 7/2011 |
| WO | 2019034320 A1 | 2/2019 |

* cited by examiner

DEVICE FOR SECURING A PERIPHERAL VENOUS CATHETER

The present application is a U.S. National Phase Application under 35 U.S.C. § 371 of PCT/ES2020/070530 filed Sep. 9, 2020, which claims priority to ES201930788 filed Sep. 10, 2019, the contents therein of the applications is incorporated by reference herein in its entirety.

TECHNICAL FIELD OF THE INVENTION

The present invention is encompassed in the field of medical devices, specifically those used to secure peripheral venous catheters, which are usually fastened in a curved or folded arrangement forming a safety loop.

BACKGROUND OF THE INVENTION

The health system requires an effective device that guarantees the safety of the peripheral venous catheter, for example, in medical emergencies.

Various devices are known that attempt to ensure the fastening of peripheral venous catheters. For example, patent document US2006047268 shows a catheter retention clamp that includes first and second straight body parts, which extend along respective longitudinal axes parallel to each other. These straight body parts are connected by an extension part extending around a 180° curve, which defines a curve of a catheter that is inserted into a U-shaped channel extending through the first straight part, the connection part and the second straight part, where the catheter is retained in the U-shaped channel by means of at least one locking closure consisting of a pair of opposing projections extending from both of the channel walls.

In a second embodiment, the pre-curved catheter clamp shown in WO2006026290 includes a body comprising first and second straight portions whose longitudinal axes are parallel to each other. The first and second straight portions are connected by an extension portion extending perpendicular to the longitudinal axes of said first and second straight portions. Where, the first and second straight portions have C-shaped cross-sections, acting as respective locking closures for the catheter that is arranged inside them as a channel.

Both embodiments have the drawback that the catheter is not secured against cross tensile loads, since it can come out through the grooves formed between the locking closures attempting to keep it inside the channel. As the cross sections of the channels are U- and C-shaped respectively, i.e., closing the channel completely is not achieved in either case, the catheter can inadvertently come out and release itself from these locking means attempting to retain it inside the channel. With this, these known solutions are not entirely effective, i.e., they are not effective and efficient, in fastening the catheter.

Similarly, patent document US5947931 discloses a catheter anchoring device, which includes a tube accessory comprising two parallel tubular segments wherein the catheter is fastened in a bent manner as a safety loop. The parallel tubular segments are interconnected by a cross segment. The first tubular segment is entirely cylindrical, while the second one comprises a groove extending therealong, where the groove allows the catheter to be coupled to the second tubular segment for fastening.

In this case, there are also the aforementioned drawbacks, i.e., through the groove, the catheter inserted in the second tubular segment can be unintentionally decoupled from it, for example, in the face of cross tensile loads, with which, this solution is also not entirely effective.

Similarly, in both known solutions, the catheter fastening means are longitudinally open and thus fail to compress the catheter in its entire perimeter, which limits the compression effectiveness of the fastening means, in such a way that it allows the movement of the catheter inside said fastening means against longitudinal tensile loads.

For this reason, a truly effective device to secure peripheral venous catheters needs to be designed, which in a simple and economical way, allows to overcome the aforementioned drawbacks.

DESCRIPTION OF THE INVENTION

The present invention is established and characterised in the independent claim, while the dependent claims describe other characteristics thereof.

The object of the invention is a device for securing a peripheral venous catheter, of the type that are usually fastened in a curved or bent arrangement, forming a safety loop. The technical problem to be solved is how to achieve a truly effective and efficient securing of the catheter, eliminating any possibility of such catheter being unintentionally decoupled from the device.

In view of the above, the device of the present invention includes a body comprising:
- a first fastening extremity,
- a second fastening extremity, and
- a connecting section, which interconnects the first fastening extremity and the second fastening extremity.

Where, the first and second fastening extremities are tubular-shaped and comprise a first longitudinal groove and a second longitudinal groove, respectively. In this way, through said longitudinal grooves, a portion of the catheter may be inserted to be fastened in a folded manner, as a safety loop, between the first and second fastening extremities.

For its part, the connecting section comprises a first portion and a second portion, which extend between the first and second longitudinal grooves; such that the first fastening extremity, the first portion of the connecting section, the second fastening extremity and the second portion of the connecting section form the body of the device with a closed perimeter outline that defines a hollow internal space.

Where, the hollow internal space is adapted to be set between a first open position and a second closed position. In this way, through the hollow internal space, in its first open position, the portion of the catheter may be inserted for attachment thereof to the first and second fastening extremities, and thus, subsequently, achieve the fastening of said portion of the catheter in the fastening extremities of the body of the device, when the hollow internal space is set in its second closed position.

Thus, by compressing the device in the horizontal direction, i.e., by the fastening extremities, the hollow internal space expands in the vertical direction, facilitating the cross insertion therein of the curved or folded portion of the catheter as a safety loop. Likewise, with the extension of the body in the vertical direction, the longitudinal grooves for access to the respective first and second fastening extremities are enlarged, facilitating the redirection of the catheter for attachment thereof to said fastening extremities. Subsequently, with the compression of the device in the vertical direction, i.e., by the portions that form its connecting section, the hollow internal space is reduced in the vertical direction, and with it, the internal tubular dimensions of the fastening extremities also decrease, between which, finally, the catheter is effectively and efficiently secured.

Additionally, it is preferred that the body comprises a strap portion adapted to secure it to the user, i.e., to the patient needing it.

As can be seen, the combination of technical characteristics included in the device object of the present application, which allow it to be shaped in a single part, give it greater effectiveness by allowing the catheter to be redirected towards the fastening extremities of the device and a perimeter securing to the latter that guarantees the total safety of the catheter against longitudinal, vertical and cross loads.

In addition, installing the catheter in the device, and in turn, the device in the patient, turns out to be quick and simple, important attributes in medical emergencies when dealing with critical, disoriented or uncooperative patients, as well as in emergencies and subsequent transfer of the patient to hospital facilities.

Likewise, securing the device to the patient is carried out without the need for additional components, and is ergonomic.

In addition, the device is inexpensive since it is made up of a single part that can be manufactured by extrusion.

BRIEF DESCRIPTION OF THE FIGURES

This specification is supplemented with a set of drawings illustrating the preferred embodiment, which are never intended to limit the invention.

DETAILED EXPLANATION OF THE INVENTION

The present invention is a device for securing a peripheral venous catheter, of the type usually fastened in a curved or folded arrangement, forming a safety loop.

Figure 1:
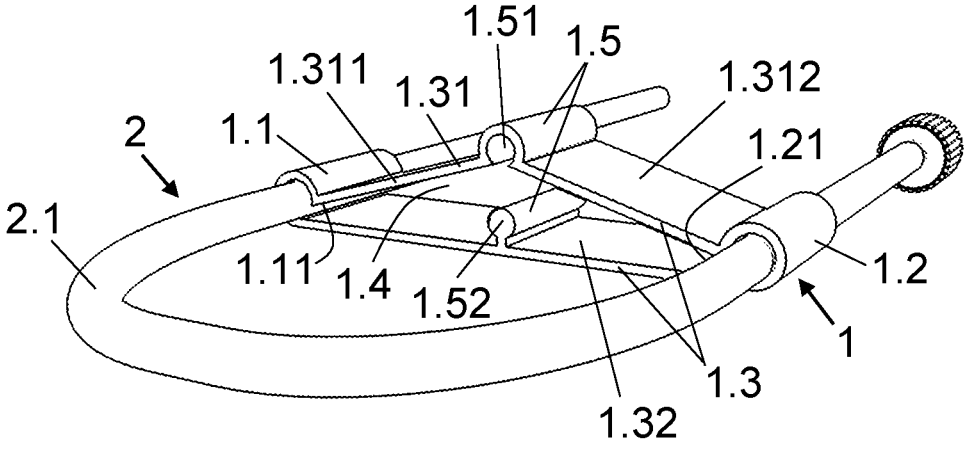
FIG. 1 represents a perspective view of the device with the hollow internal space set in its open position.
Figure 2:
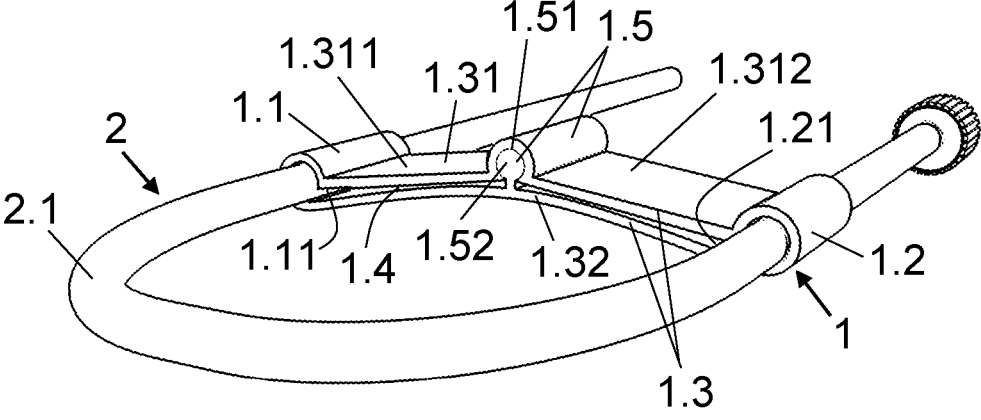
FIG. 2 represents a perspective view of the device with the hollow internal space set in its closed position.

As shown in FIGS. 1 and 2, the device includes a body (1) comprising:

a first fastening extremity (1.1), a second fastening extremity (1.2) and a connecting section (1.3) that interconnects the first fastening extremity (1.1) and the second fastening extremity (1.2).

Preferably, the body (1) comprises a constant cross section throughout its length and, further, it can advantageously be manufactured with a flexible material, for example, polypropylene or nylon.

The first and second fastening extremities (1.1, 1.2) are tubular-shaped and comprise a first longitudinal groove (1.11) and a second longitudinal groove (1.21) respectively, in such a way that through said longitudinal grooves (1.11, 1.21) a portion of the catheter (2) may be inserted to be fastened in a folded manner, as a safety loop (2.1), between said first and second fastening extremities (1.1, 1.2).

For its part, the connecting section (1.3) comprises a first portion (1.31) and a second portion (1.32) extending between the first and second longitudinal grooves (1.11, 1.21), such that the first fastening extremity (1.1), the first portion (1.31) of the connecting section (1.3), the second fastening extremity (1.2) and the second portion (1.32) of the connecting section (1.3) form the body (1) with a closed perimeter outline, which guarantees the safety of the portion of the catheter (2) against possible vertical and/or cross loads to which it may be subjected during use.

Additionally, it is preferred that the first portion (1.31) of the connecting section (1.3) has a greater length than its second portion (1.32). For example, the first portion (1.31) could be formed by two sub-portions (1.311, 1.312) which, with the second portion (1.32), form the triangular-shaped closed perimeter outline. Where, between the sub-portions (1.311, 1.312) an obtuse angle is formed, and between said sub-portions (1.311, 1.312) and the second portion (1.32) respective acute angles are formed, in such a way that a progressive and smooth transition of the portion of the catheter (2) to the inside of the respective fastening extremities (1.1, 1.2) is facilitated.

In any case, the closed perimeter outline defines a hollow internal space (1.4) adapted to be set between a first open position (seen in FIG. 1) and a second closed position (seen in FIG. 2).

Thus, through the hollow internal space (1.4), in its first open position, the portion of the catheter (2) may be inserted for attachment thereof to the first and second fastening extremities (1.1, 1.2). To do this, in this first position, the internal diameters of the fastening extremities (1.1, 1.2) turn out to be greater than or equal to the external diameter of the catheter (2), facilitating the insertion and attachment of the latter to said fastening extremities (1.1, 1.2).

Then, by arranging the hollow internal space (1.4) in its second closed position, said portion of the catheter (2) is fastened in the first and second fastening extremities (1.1, 1.2). To do this, said fastening extremities (1.1, 1.2) close reducing their dimensions until they comprise respective internal diameters that correspond to the external diameter of the catheter (2), or even better, smaller dimensions; in any case, they achieve a compression value on said catheter (2) that guarantees its immobilisation without strangling it.

Thus, in the second closed position, the fastening extremities (1.1, 1.2) are completely closed, compressing the catheter (2) in its entire perimeter, achieving 100% immobilisation thereof against any type of tensile loads, either longitudinal, vertical or crosswise. In other words, the inadvertent extraction or decoupling of the catheter (2) is prevented, as well as its sliding inside the fastening extremities (1.1, 1.2).

Likewise, it is preferred that the device comprises anchoring means (1.5) from the first portion (1.31) to the second portion (1.32) of the connecting section (1.3), which, as shown in FIG. 2, are adapted to maintain the hollow internal space (1.4) of the body (1) in its second closed position.

For example, the anchoring means (1.5) could be a tongue-and-groove joint. Preferably, the tongue-and-groove joint (1.5) comprises a first recess-shaped part (1.51), arranged flush between the sub-portions (1.311, 1.312) of the first portion (1.31) of the connecting section (1.3), and a second projection-shaped part (1.52) arranged raised from a centre of the second portion (1.32).

For example, the first recess-shaped part (1.51) of the tongue-and-groove joint (1.5) could have a tubular geometry, and its second projection-shaped part (1.52) could have a cylindrical geometry, and engage together in an adjusted manner.

Thus, with the anchoring of the tongue-and-groove joint (1.5), maintaining the closure of the hollow internal space (1.4) of the body (1) is achieved, i.e., set in its second position, and thereby locking the fastening extremities (1.1, 1.2) that retain the portion of the catheter (2), which, being locked, cannot open against the occurrence of a load, whether longitudinal, vertical or crosswise, and accordingly, the portion of the catheter (2) cannot move in any direction inside the fastening extremities (1.1, 1.2). In addition, thanks to this locking, said fastening extremities (1.1, 1.2) can be kept with an internal diameter that guarantees an accurate compression value on the catheter (2) that allows its retention and that does not vary with the possible loads to which may it be subjected during use.

In the same way, it is preferred that the first fastening extremity (1.1) and the second fastening extremity (1.2) are arranged raised on the second portion (1.32) of the connecting section (1.3). Thus, once the tongue-and-groove joint that forms the anchoring means (1.5) has been coupled, as shown in FIG. 2, the second portion (1.32) becomes concavely arched, being an ergonomic shape for the user, for example, a patient, to whom the device is coupled.

Thus, the anchoring means (1.5) achieve:

compressing the portion of the catheter (2), with a view to guaranteeing its safety against any type of load, and providing the lower part (second portion (1.32) of the connecting section (1.3)) of the body (1) with an ergonomic shape for its installation, for example, on a patient's arm.

Figure 3:
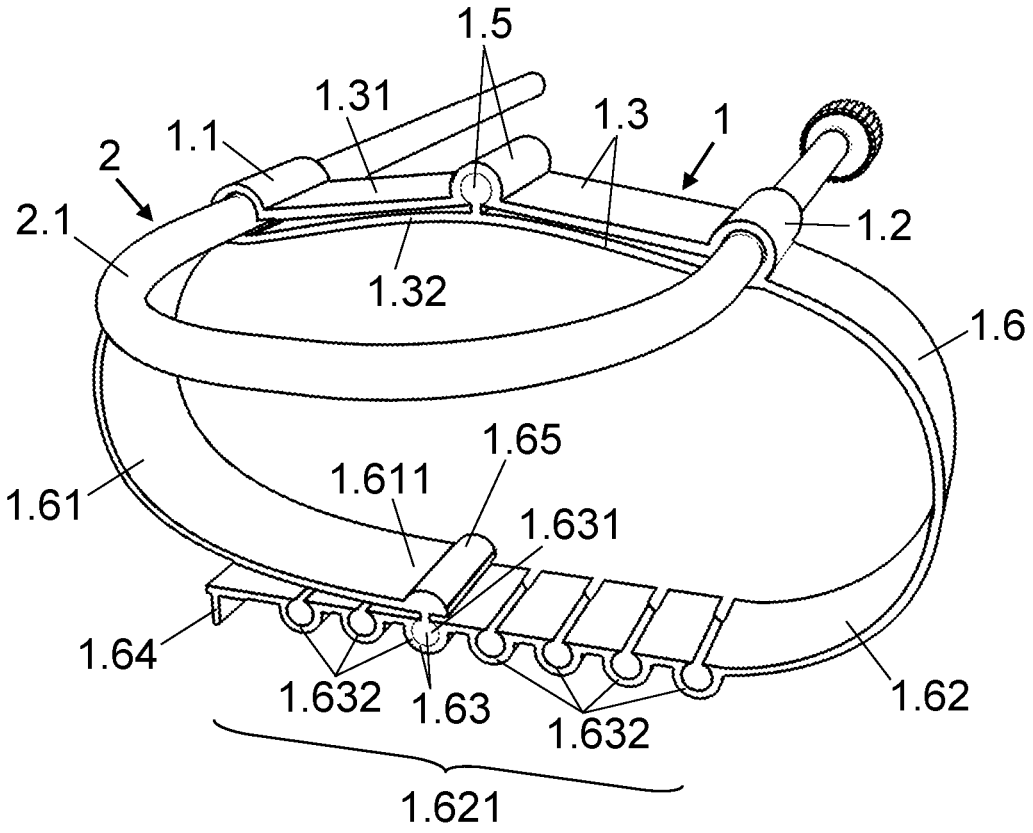
FIG. 3 represents a perspective view of a second embodiment of the device of FIGS. 1 and 2, with a strap for securing it to the user.
Figure 4:
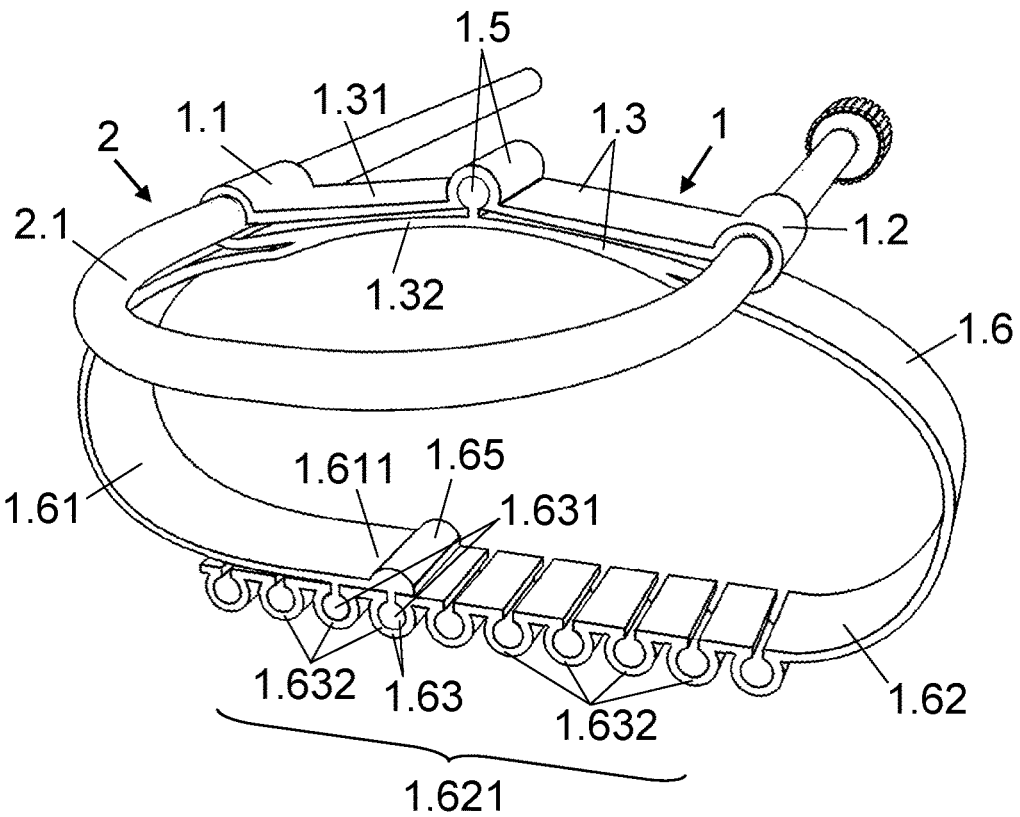
FIG. 4 represents a perspective view of a third embodiment of the device of FIGS. 1 and 2, with a strap for securing it to the user.

On the other hand, as shown in FIGS. 3 and 4, advantageously, the body (1) can comprise a strap portion (1.6) adapted to secure the body (1) to the user.

Preferably, the strap portion (1.6) is integrated into the body (1) as respective first and second side prolongations (1.61, 1.62) of the second portion (1.32) of the connecting section (1.3). Either, as shown in FIG. 3, the first and second side prolongations (1.61, 1.62) extending in an integrated manner from the respective fastening extremities (1.1, 1.2); or, as shown in FIG. 4, the first and second side prolongations (1.61, 1.62) can extend below the second portion (1.32) of the connecting section (1.3). With this last embodiment, greater ergonomics is achieved in securing the device to the user, since the body (1) is arranged above the strap portion (1.6), without direct contact with the user.

Likewise, it is preferred that the strap portion (1.6) comprises adjustment means (1.63) to adjust the body (1) to the user.

Preferably, the adjustment means (1.63) could be a second tongue-and-groove joint comprising:

at least one first projection-shaped portion (1.631) arranged raised on a first free end (1.611) of the first side prolongation (1.61) of the strap portion (1.6), and a plurality of second recess-shaped portions (1.632) arranged in a row flush with a second free end (1.621) of the second side prolongation (1.62) of the strap portion (1.6).

In such a way that, by engaging a single first projection-shaped portion (1.631), see the embodiment of FIG. 3, or several first projection-shaped portions (1.631), see the embodiment of FIG. 4, in respective second recess-shaped portions (1.632) the adjustment and fastening of the body (1) onto the user is achieved. Obviously, the more first projection-shaped portions (1.631) are configured in the first side prolongation (1.61) to engage in respective second recess-shaped portions (1.632) of the second side prolongation (1.62), the more robust and secure will be the securing of the strap portion (1.6) to the user.

In any case, the degree of compression of the device, for example on the patient's arm, can be very easily and quickly regulated.

Additionally, as shown in FIG. 3, the strap portion (1.6) could comprise a puller projection (1.64), arranged at the second free end (1.621), whose function is to facilitate handling of the second side prolongation (1.62) at the time of assembling or disassembling the adjustment means (1.63); and a protective projection (1.65), arranged at the first free end (1.611) of the first side prolongation (1.62), whose function is to prevent said first free end (1.611) from causing any damage to the patient's skin.

Figure 5:
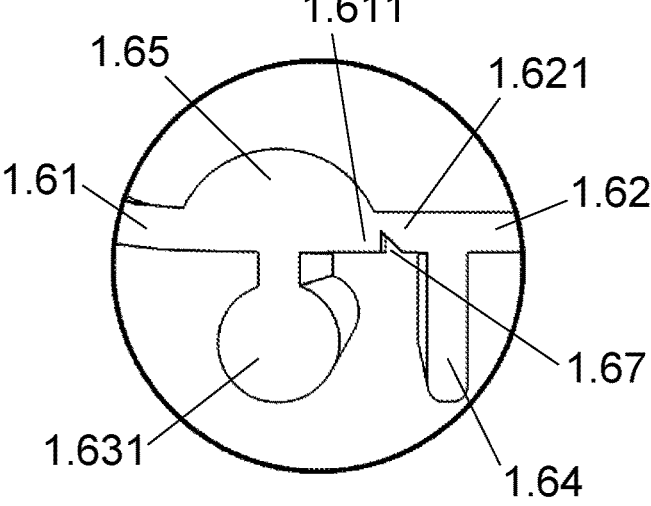
FIG. 5 represents an enlarged view of the securing strap of the device of any of FIG. 3 or 4, showing how the fastening strap can be closed around the perimeter to facilitate its manufacture, and then can be cut for installation on the user.

Advantageously, as shown in FIG. 5, the strap portion (1.6) could be formed in a closed perimeter manner, with a view to facilitating its manufacture. For example, with the first free end (1.611) of the first side prolongation (1.61) integral with the second free end (1.621) of the second side prolongation (1.62) of the strap portion (1.6). Subsequently, when it is to be installed on the user, the first and second free ends (1.611, 1.621) are separated by making a cut, for example, in a slit (1.67) formed between said first and second free ends (1.611, 1.621).

The invention claimed is:

1. A device for securing a peripheral venous catheter, which includes an integral body (1) comprising a first fastening extremity (1.1), a second fastening extremity (1.2) and a connecting section (1.3) that interconnects the first fastening extremity (1.1) and the second fastening extremity (1.2), the first and second fastening extremities (1.1, 1.2) are tubular-shaped and comprise a first longitudinal groove (1.11) and a second longitudinal groove (1.21) respectively, such that through said first and second longitudinal grooves (1.11, 1.21) a portion of the catheter (2) may be inserted to be fastened in a folded manner as a safety loop (2.1) between the first and second fastening extremities (1.1, 1.2), wherein the connecting section (1.3) comprises a first portion (1.31) and a second portion (1.32) extending between the first and second longitudinal grooves (1.11, 1.21), in such a way that the first fastening extremity (1.1), the first portion (1.31) of the connecting section (1.3), the second fastening extremity (1.2) and the second portion (1.32) of the connecting section (1.3) form the body (1) with a contiguous closed perimeter outline that defines a contiguous hollow internal space (1.4) adapted to be set between a first open position and a second closed position, where, through the hollow internal space (1.4), in the first open position, the portion of the catheter (2) may be inserted for attachment thereof to the first and second fastening extremities (1.1, 1.2), and said portion of the catheter (2) being fastened at said first and second fastening extremities (1.1, 1.2) by arranging the hollow internal space (1.4) in the second closed position, wherein anchoring means from the first portion (1.31) to the second portion (1.32) of the connecting section (1.3), adapted to maintain the hollow internal space (1.4) of the body (1) in the second closed position, are a tongue-and-groove joint (1.5), wherein the tongue-and-groove joint (1.5) comprises a first recess-shaped part (1.51) arranged flush between sub-portions (1.311, 1.312) of the first portion (1.31) of the connecting section (1.3), and a second projection-shaped part (1.52) arranged raised from a centre of the second portion (1.32).

2. The device according to claim 1, wherein the first portion (1.31) of the connecting section (1.3) has a greater length than the second portion (1.32).

3. The device according to claim 2, wherein the two sub-portions (1.311, 1.312) of the first portion (1.31) and the second portion (1.32) form a triangular-shaped closed perimeter outline.

4. The device according to claim 1, wherein the first recess-shaped part (1.51) of the tongue-and-groove joint (1.5) has a tubular geometry and the second projection-shaped part (1.52) has a cylindrical geometry.

5. The device according to claim 1, wherein the integral body (1) comprises a constant cross section throughout a length.

6. The device according to claim 1, wherein, in the second closed position of the hollow internal space (1.4), the first fastening extremity (1.1) and the second fastening extremity (1.2) comprise respective internal diameters equal to or less than an external diameter of the catheter (2), where the internal diameters of said first and second fastening extremities (1.1, 1.2) generate a compression value on the catheter (2) that guarantees the immobilisation of said catheter (2) without strangling the catheter (2).

7. The device according to claim 1, wherein the first fastening extremity (1.1) and the second fastening extremity (1.2) are arranged raised on the second portion (1.32) of the connecting section (1.3).

8. The device according to claim 1, wherein the integral body (1) comprises a strap portion (1.6) adapted to secure the body (1) to a user.

9. The device according to claim 8, wherein the strap portion (1.6) is integrated into the integral body (1) as respective first and second side prolongations (1.61, 1.62) of the second portion (1.32) of the connecting section (1.3).

10. The device according to claim 9, wherein the first and second side prolongations (1.61, 1.62) extend below the second portion (1.32) of the connecting section (1.3).

11. The device according to claim 8, wherein the strap portion (1.6) comprises adjustment means (1.63) to adjust the integral body (1) to the user.

12. The device according to claim 11, wherein the adjustment means (1.63) are a second tongue-and-groove joint comprising at least one first projection-shaped portion (1.631) arranged raised on a first free end (1.611) of a first side prolongation (1.61) of the strap portion (1.6), and a plurality of second recess-shaped portions (1.632) arranged in a row flush with a second free end (1.621) of a second side prolongation (1.62) of the strap portion (1.6).

\*     \*     \*     \*     \*